(12) United States Patent
Root et al.

(10) Patent No.: US 10,835,283 B2
(45) Date of Patent: Nov. 17, 2020

(54) CATHETER

(71) Applicant: Teleflex Life Sciences Limited, Valletta (MT)

(72) Inventors: Howard C. Root, Excelsior, MN (US); John Bridgeman, Minneapolis, MN (US); Steve Michael, New Hope, MN (US); Gregg S. Sutton, Orono, MN (US); Karl V. Ganske, Edina, MN (US)

(73) Assignee: Teleflex Life Sciences Limited, Valletta (MT)

( * ) Notice: Subject to any disclaimer, the term of this patent is extended or adjusted under 35 U.S.C. 154(b) by 0 days.

(21) Appl. No.: 15/441,352

(22) Filed: Feb. 24, 2017

(65) Prior Publication Data

US 2017/0156750 A1   Jun. 8, 2017

Related U.S. Application Data

(62) Division of application No. 14/673,966, filed on Mar. 31, 2015, now Pat. No. 9,636,477.

(Continued)

(51) Int. Cl.
*A61B 17/3207* (2006.01)
*A61M 25/00* (2006.01)
*A61M 25/01* (2006.01)

(52) U.S. Cl.
CPC ... *A61B 17/320758* (2013.01); *A61M 25/005* (2013.01); *A61M 25/0043* (2013.01);
(Continued)

(58) Field of Classification Search
CPC ........ A61M 2025/006; A61M 25/0043; A61M 25/0045; A61M 25/005; A61B 17/320758
See application file for complete search history.

(56) References Cited

U.S. PATENT DOCUMENTS

| 3,815,608 A | 6/1974 | Hodgson et al. |
| 4,898,212 A | 2/1990 | Searfoss et al. |

(Continued)

FOREIGN PATENT DOCUMENTS

| DE | 69424027 | 9/2000 |
| EP | 0517075 A1 | 12/1992 |

(Continued)

OTHER PUBLICATIONS

Notice of Allowance dated Mar. 23, 2017, in U.S. Appl. No. 14/673,966, filed Mar. 31, 2015.

(Continued)

*Primary Examiner* — Quynh-Nhu H. Vu
(74) *Attorney, Agent, or Firm* — Gregory A. Smock; Robert B. Madden

(57) ABSTRACT

Catheters and methods for supporting a guidewire or delivering a radiopaque, diagnostic or therapeutic agent through a vessel stenosis or other tortuous anatomy are disclosed. A catheter can comprise an elongate shaft body and a tip member disposed at a distal end of the shaft body. The shaft body can extend from a proximal end to the distal end and can define an inner lumen. The shaft body can include a liner, a braid member surrounding the liner, a multi-layer coil surrounding the braid member, and a polymer cover surrounding the multi-layer coil. The multi-layer coil can include first and second coil layers wound in opposing directions. An outer surface portion of the polymer cover can include one or more helical threads. In an example, the one or more helical threads are positioned around a distal end portion of the shaft body. The tip member can be made from a metal or a polymer and can also include one or more helical threads around its outer surface.

21 Claims, 6 Drawing Sheets

Related U.S. Application Data

(60) Provisional application No. 62/061,781, filed on Oct. 9, 2014.

(52) U.S. Cl.
CPC .... *A61M 25/0045* (2013.01); *A61M 25/0105* (2013.01); *A61M 2025/006* (2013.01)

(56) References Cited

U.S. PATENT DOCUMENTS

| | | | |
|---|---|---|---|
| 4,947,864 | A * | 8/1990 | Shockey .......... A61M 25/0172 600/434 |
| 5,037,404 | A | 8/1991 | Gold et al. |
| 5,057,092 | A | 10/1991 | Webster |
| 5,129,910 | A | 7/1992 | Phan et al. |
| 5,183,079 | A | 2/1993 | Blin |
| 5,263,959 | A | 11/1993 | Fischell |
| 5,423,846 | A | 6/1995 | Fischell |
| 5,454,795 | A | 10/1995 | Samson |
| 5,462,523 | A | 10/1995 | Samson et al. |
| 5,554,139 | A | 9/1996 | Okajima |
| 5,569,218 | A | 10/1996 | Berg |
| 5,569,220 | A | 10/1996 | Webster |
| 5,591,142 | A | 1/1997 | Erp |
| 5,601,537 | A | 2/1997 | Frassica |
| 5,658,264 | A | 8/1997 | Samson |
| 5,662,622 | A | 9/1997 | Gore et al. |
| 5,681,296 | A | 10/1997 | Ishida |
| 5,695,483 | A | 12/1997 | Samson |
| 5,702,373 | A | 12/1997 | Samson |
| 5,769,830 | A | 6/1998 | Parker |
| 5,792,124 | A | 8/1998 | Harrigan et al. |
| 5,853,400 | A | 12/1998 | Samson |
| 5,871,475 | A | 2/1999 | Frassica |
| 5,871,537 | A | 2/1999 | Holman et al. |
| 5,876,385 | A | 3/1999 | Ikari et al. |
| 5,876,386 | A | 3/1999 | Samson |
| 5,885,508 | A | 3/1999 | Ishida |
| 5,891,114 | A | 4/1999 | Chien et al. |
| 5,897,537 | A | 4/1999 | Berg et al. |
| 5,911,715 | A | 6/1999 | Berg et al. |
| 5,927,345 | A | 7/1999 | Samson |
| 5,951,539 | A | 9/1999 | Nita et al. |
| 5,968,064 | A | 10/1999 | Selmon et al. |
| 6,003,561 | A | 12/1999 | Brindza et al. |
| 6,053,903 | A | 4/2000 | Samson |
| 6,059,823 | A | 5/2000 | Holman et al. |
| 6,143,013 | A | 11/2000 | Samson et al. |
| 6,165,163 | A | 12/2000 | Chien et al. |
| 6,171,297 | B1 | 1/2001 | Pedersen et al. |
| 6,217,565 | B1 | 4/2001 | Cohen |
| 6,231,546 | B1 | 5/2001 | Milo et al. |
| 6,235,000 | B1 | 5/2001 | Milo et al. |
| 6,245,098 | B1 | 6/2001 | Feeser et al. |
| 6,319,276 | B1 | 11/2001 | Holman et al. |
| 6,368,316 | B1 | 4/2002 | Jansen et al. |
| 6,485,457 | B1 | 11/2002 | Hisamatsu et al. |
| 6,508,804 | B2 | 1/2003 | Sarge et al. |
| 6,508,806 | B1 | 1/2003 | Hoste |
| 6,508,825 | B1 | 1/2003 | Selmon et al. |
| 6,511,458 | B2 | 1/2003 | Milo et al. |
| 6,511,462 | B1 | 1/2003 | Itou et al. |
| 6,533,754 | B1 | 3/2003 | Hisamatsu et al. |
| 6,589,227 | B2 | 7/2003 | Henrik |
| 6,638,247 | B1 | 10/2003 | Selmon et al. |
| 6,652,692 | B2 | 11/2003 | Pedersen et al. |
| 6,689,120 | B1 | 2/2004 | Gerdts |
| 6,692,523 | B2 | 2/2004 | Holman et al. |
| 6,719,725 | B2 | 4/2004 | Milo et al. |
| 6,726,712 | B1 | 4/2004 | Raeder-Devens et al. |
| 6,824,553 | B1 | 11/2004 | Samson et al. |
| 6,858,024 | B1 | 2/2005 | Berg et al. |
| 6,926,721 | B2 | 8/2005 | Basta |
| 6,966,891 | B2 | 11/2005 | Ookubo et al. |
| 7,025,758 | B2 | 4/2006 | Klint |
| 7,037,288 | B2 | 5/2006 | Rosenberg et al. |
| 7,104,966 | B2 | 9/2006 | Shiber |
| 7,104,979 | B2 | 9/2006 | Jansen et al. |
| 7,117,703 | B2 | 10/2006 | Kato et al. |
| 7,155,272 | B2 | 12/2006 | Yamaguchi et al. |
| 7,166,100 | B2 | 1/2007 | Jordan et al. |
| 7,291,127 | B2 | 11/2007 | Eidenschink |
| 7,297,302 | B2 | 11/2007 | Berg et al. |
| 7,300,534 | B2 | 11/2007 | Wang et al. |
| 7,322,988 | B2 | 1/2008 | Sterud et al. |
| 7,354,430 | B2 | 4/2008 | Pepin |
| 7,434,437 | B2 | 10/2008 | Kato et al. |
| 7,488,338 | B2 | 2/2009 | Eidenschink |
| 7,491,230 | B2 | 2/2009 | Holman et al. |
| 7,494,478 | B2 | 2/2009 | Itou et al. |
| 7,579,550 | B2 | 8/2009 | Dayton et al. |
| 7,597,830 | B2 | 10/2009 | Zhou |
| 7,615,043 | B2 | 11/2009 | Zhou |
| 7,621,904 | B2 | 11/2009 | McFerran et al. |
| 7,674,411 | B2 | 3/2010 | Berg et al. |
| 7,699,790 | B2 | 4/2010 | Simpson |
| 7,704,245 | B2 | 4/2010 | Dittman et al. |
| 7,740,652 | B2 | 6/2010 | Gerdts et al. |
| 7,758,624 | B2 | 7/2010 | Dorn |
| 7,763,012 | B2 | 7/2010 | Petrick et al. |
| 7,766,896 | B2 | 8/2010 | Volk et al. |
| 7,771,444 | B2 | 8/2010 | Patel et al. |
| 7,785,365 | B2 | 8/2010 | Holman et al. |
| 7,799,068 | B2 | 9/2010 | Holman et al. |
| 7,803,169 | B2 | 9/2010 | Shamay |
| 7,815,599 | B2 | 10/2010 | Griffin et al. |
| 7,824,392 | B2 | 11/2010 | Zhou |
| 7,828,790 | B2 | 11/2010 | Griffin |
| 7,841,994 | B2 | 11/2010 | Skujins et al. |
| 7,854,755 | B2 | 12/2010 | Lafontaine et al. |
| 7,871,430 | B2 | 1/2011 | Pavcnik et al. |
| 7,887,529 | B2 | 2/2011 | Eder |
| 7,896,861 | B2 | 3/2011 | McFerran et al. |
| 7,909,779 | B2 | 3/2011 | Shimogami et al. |
| 7,909,812 | B2 | 3/2011 | Jansen et al. |
| 7,914,515 | B2 | 3/2011 | Heideman et al. |
| 7,914,520 | B2 | 3/2011 | Kennedy, II |
| 7,927,784 | B2 | 4/2011 | Simpson |
| 7,955,313 | B2 | 6/2011 | Boismier |
| 7,968,038 | B2 | 6/2011 | Dittman et al. |
| 7,981,091 | B2 * | 7/2011 | Root .............. A61M 25/0068 604/264 |
| 7,985,213 | B2 | 7/2011 | Parker |
| 7,985,214 | B2 | 7/2011 | Garabedian et al. |
| 7,998,132 | B2 | 8/2011 | Gregorigh et al. |
| 8,021,352 | B2 | 9/2011 | Slazas et al. |
| 8,092,509 | B2 | 1/2012 | Dorn |
| 8,109,872 | B2 | 2/2012 | Kennedy, II et al. |
| 8,109,985 | B2 | 2/2012 | Meyer et al. |
| 8,118,804 | B2 | 2/2012 | Takagi et al. |
| 8,124,876 | B2 | 2/2012 | Dayton et al. |
| 8,172,863 | B2 | 5/2012 | Robinson et al. |
| 8,202,246 | B2 | 6/2012 | Kugler et al. |
| 8,206,373 | B2 | 6/2012 | Zhou |
| 8,221,387 | B2 | 7/2012 | Shelso et al. |
| 8,226,702 | B2 | 7/2012 | Raeder-Devens et al. |
| 8,231,647 | B2 | 7/2012 | Eidenschink |
| 8,235,942 | B2 | 8/2012 | Frassica et al. |
| 8,251,976 | B2 | 8/2012 | Zhou |
| 8,257,314 | B2 | 9/2012 | Agnew |
| 8,303,570 | B2 | 11/2012 | Gregorich et al. |
| 8,317,772 | B2 | 11/2012 | Jansen et al. |
| 8,328,791 | B2 | 12/2012 | Griffin |
| 8,337,425 | B2 | 12/2012 | Olson et al. |
| 8,366,674 | B2 | 2/2013 | Frassica et al. |
| 8,372,056 | B2 | 2/2013 | Eder |
| 8,377,035 | B2 | 2/2013 | Zhou et al. |
| 8,382,739 | B2 | 2/2013 | Walak |
| 8,387,347 | B2 | 3/2013 | Imai et al. |
| 8,403,912 | B2 | 3/2013 | McFerran et al. |
| 8,414,477 | B2 | 4/2013 | Tallarida et al. |
| 8,419,658 | B2 | 4/2013 | Eskuri |
| 8,454,578 | B2 | 6/2013 | Leeflang et al. |

(56) References Cited

U.S. PATENT DOCUMENTS

| | | |
|---|---|---|
| 8,486,010 B2 | 7/2013 | Nomura |
| 8,496,679 B2 | 7/2013 | Robinson et al. |
| 8,500,785 B2 | 8/2013 | Gunderson |
| 8,523,841 B2 | 9/2013 | Itou et al. |
| 8,535,369 B2 | 9/2013 | Raeder-Devens et al. |
| 8,540,695 B2 | 9/2013 | Shimogami et al. |
| D690,806 S | 10/2013 | Nakayama et al. |
| 8,551,073 B2 | 10/2013 | Katoh et al. |
| 8,556,914 B2 | 10/2013 | Vrba |
| 8,574,219 B2 | 11/2013 | Adams et al. |
| 8,603,066 B2 | 12/2013 | Heidman et al. |
| 8,764,631 B2 | 7/2014 | Frassica |
| 8,870,755 B2 | 10/2014 | Frassica et al. |
| 8,955,552 B2 | 2/2015 | Nanney et al. |
| 9,636,477 B2 | 5/2017 | Root et al. |
| 9,782,561 B2 | 10/2017 | Kugler et al. |
| 10,238,834 B2 | 3/2019 | Bridgeman et al. |
| 2002/0032408 A1* | 3/2002 | Parker .............. A61L 29/02 604/103.09 |
| 2002/0107506 A1 | 8/2002 | McGuckin et al. |
| 2002/0156460 A1* | 10/2002 | Ye .............. A61L 29/085 604/534 |
| 2003/0097138 A1 | 5/2003 | Reydel |
| 2003/0191451 A1 | 10/2003 | Gilmartin |
| 2004/0002677 A1 | 1/2004 | Gentsler |
| 2004/0087885 A1 | 5/2004 | Kawano et al. |
| 2004/0102719 A1* | 5/2004 | Keith .............. A61M 25/01 600/585 |
| 2005/0021002 A1 | 1/2005 | Deckman et al. |
| 2005/0171478 A1 | 8/2005 | Selmon et al. |
| 2005/0222585 A1 | 10/2005 | Miyata et al. |
| 2006/0100602 A1 | 5/2006 | Klint |
| 2006/0151043 A1 | 7/2006 | Nanney et al. |
| 2006/0258987 A1 | 11/2006 | Lentz et al. |
| 2006/0264904 A1 | 11/2006 | Kerby et al. |
| 2007/0010863 A1* | 1/2007 | Stenzel .............. A61M 29/02 623/1.1 |
| 2007/0060996 A1 | 3/2007 | Goodin et al. |
| 2007/0208221 A1 | 9/2007 | Kennedy et al. |
| 2007/0260224 A1 | 11/2007 | Oepen et al. |
| 2008/0039823 A1 | 2/2008 | Shimogami et al. |
| 2008/0108974 A1 | 5/2008 | Roth |
| 2008/0185063 A1 | 8/2008 | Bieszczad et al. |
| 2009/0048657 A1 | 2/2009 | Duran et al. |
| 2009/0112063 A1 | 4/2009 | Bakos et al. |
| 2009/0124899 A1 | 5/2009 | Jacobs et al. |
| 2009/0312831 A1 | 12/2009 | Dorn |
| 2010/0069718 A1* | 3/2010 | Frassica .......... A61B 17/12099 600/137 |
| 2010/0076264 A1 | 3/2010 | Tallarida et al. |
| 2010/0094258 A1* | 4/2010 | Shimogami ......... A61M 25/005 604/527 |
| 2010/0256727 A1 | 10/2010 | Gerdts et al. |
| 2010/0268243 A1* | 10/2010 | Parker .............. A61F 2/95 606/108 |
| 2010/0297334 A1 | 11/2010 | Weber |
| 2011/0009889 A1 | 1/2011 | Shamay |
| 2011/0035927 A1 | 2/2011 | Griffin et al. |
| 2011/0257042 A1 | 10/2011 | Simpson |
| 2011/0297307 A1 | 12/2011 | Slazas et al. |
| 2012/0016344 A1 | 1/2012 | Kusakabe |
| 2012/0116491 A1 | 5/2012 | Meyer et al. |
| 2012/0136340 A1 | 5/2012 | Tanioka |
| 2012/0149985 A1 | 6/2012 | Frassica et al. |
| 2012/0209302 A1* | 8/2012 | Carley .............. A61M 25/0009 606/159 |
| 2012/0271174 A1 | 10/2012 | Iwahashi |
| 2012/0323251 A1 | 12/2012 | Kugler et al. |
| 2013/0018318 A1* | 1/2013 | Ravichandran ... A61M 25/0012 604/172 |
| 2013/0023858 A1 | 1/2013 | Dayton et al. |
| 2013/0053766 A1 | 2/2013 | Hollett |
| 2013/0072905 A1 | 3/2013 | Jansen et al. |
| 2013/0096535 A1 | 4/2013 | Gregorigh et al. |
| 2013/0110144 A1 | 5/2013 | Olson et al. |
| 2013/0116721 A1 | 5/2013 | Takagi et al. |
| 2013/0137977 A1 | 5/2013 | Eder |
| 2013/0150808 A1 | 6/2013 | Ogle et al. |
| 2013/0296907 A1 | 11/2013 | Robinson et al. |
| 2013/0331820 A1 | 12/2013 | Itou et al. |
| 2015/0051541 A1 | 2/2015 | Kanemasa et al. |
| 2016/0101261 A1 | 4/2016 | Kugler et al. |
| 2016/0101262 A1 | 4/2016 | Root et al. |
| 2016/0346508 A1 | 12/2016 | Williams et al. |
| 2019/0167943 A1 | 6/2019 | Bridgeman et al. |

FOREIGN PATENT DOCUMENTS

| | | |
|---|---|---|
| EP | 0661072 A1 | 7/1995 |
| EP | 1096965 B1 | 12/2007 |
| JP | 07323090 A | 12/1995 |
| JP | 2000014764 A | 1/2000 |
| JP | 2001501846 A | 2/2001 |
| JP | 3659664 B2 | 6/2005 |
| JP | 2007029120 A | 2/2007 |
| JP | 2007061311 A | 3/2007 |
| JP | 2014097090 A1 | 5/2014 |
| JP | 2015033501 A | 2/2015 |
| KR | 101314714 B1 | 10/2013 |
| WO | 1998015311 A1 | 4/1998 |
| WO | 2005105192 A1 | 11/2005 |

OTHER PUBLICATIONS

PCT Application No. PCT/IB2018/054054 partial search report dated Sep. 28, 2018.

European appln. No. 19163614.1 European Search Report dated Jun. 17, 2019.

Japanese Office Action dated Feb. 3, 2020, in Japanese application No. JP 2019-042568.

* cited by examiner

CATHETER

CLAIM OF PRIORITY

This non-provisional patent document is a divisional of U.S. patent application Ser. No. 14/673,966, filed on Mar. 31, 2015, which claims the benefit of priority under 35 U.S.C. § 119(e) to U.S. Provisional Patent Application Ser. No. 62/061,781, entitled "CATHETER," filed on Oct. 9, 2014, both of which are herein incorporated by reference in their entirety.

TECHNICAL FIELD

The subject matter of this patent document relates to the field of medical devices. More particularly, but not by way of limitation, the subject matter relates to catheters and methods for supporting a guidewire or delivering a radiopaque, diagnostic or therapeutic agent.

BACKGROUND

A variety of catheters exist for percutaneous insertion into a subject's vascular system to accomplish diagnostic or therapeutic objectives using the Seldinger technique. As part of the Seldinger technique, a guidewire can be inserted through the lumen of a hollow needle and made to enter the vascular system. A catheter can fit over and slide along the guidewire as it passes through vasculature. The guidewire alone or with the help of the catheter can be incrementally maneuvered through the vasculature to a target site.

Catheters are typically introduced through a large artery, such as those found in the groin or neck, and then passed through ever-narrower regions of the vascular system until reaching the target site. Often, such pathways will wind back upon themselves in a multi-looped path. The quest to provide treatment options for narrowing and winding vessels and other lumens has given rise to the need to reduce catheter size, yet retain a catheter's favorable structural properties.

OVERVIEW

Various structural properties can be used to describe catheters. "Pushability," for example, can be used to describe a catheter's axial strength to facilitate movement of its distal end through vascular passages or other body lumens by applying an axial pushing force near its proximal end. A related characteristic, "torqueability," can be used to describe the ability to rotate the catheter's distal end by rotating its proximal end. "Flexibility," particularly along a distal portion of the catheter, becomes increasingly important as the catheter enters winding or tortuous passages. Another characteristic that becomes more important with increased curvature of passages is the ability to resist kinking.

The present inventors recognize a difficulty in placing existing "push-to-advance" catheter designs, which include a relatively stiff, thick wall to navigate a vascular passage. The present inventors further recognize that as higher demands for length have been placed on catheters, a competing difficulty of smaller catheter distal end portions has developed.

The present catheters overcome drawbacks of existing catheter designs by providing a structure that, despite a reduction in distal diameter, maintains favorable structural properties and advanceability along its length. A catheter can comprise an elongate shaft body and a tip member disposed at a distal end of the shaft body. The shaft body can extend from a proximal end to the distal end and can define an inner lumen. The shaft body can include a liner, a braid member surrounding the liner, a multi-layer coil surrounding the braid member, and a polymer cover surrounding the multi-layer coil. The multi-layer coil can include first and second coil layers wound in opposing directions. An outer surface portion of the polymer cover can include one or more helical threads. In an example, the one or more helical threads are positioned around a distal end portion of the shaft body and have a radial height sufficient to provide a longitudinal pull on a vessel wall or a stenosis when rotated. The tip member can be made from a metal or a polymer and can also include one or more helical threads around its outer surface. Clinical bench testing has demonstrated that the present catheters exhibit pushability, flexibility, an ability to transfer torque in a controllable manner without kinking, and an ability to be propelled along a blood vessel, particularly when rotated.

The present methods can include advancing a distal end of a guidewire to a location proximate a stenosis or other narrowing in a blood vessel; guiding a catheter over the guidewire; using the guidewire as a rail, advancing a distal end of the catheter to the location proximate the stenosis or narrowing; rotating the catheter in a first direction and advancing it into the stenosis or narrowing; and advancing the guidewire through the stenosis or narrowing with the support of the catheter. The guidewire can be inserted into an inner lumen of the catheter, where the inner lumen is defined, in part, by a liner, a braid member surrounding the liner, a multi-layer coil surrounding the braid member, and a polymer cover surrounding the multi-layer coil. Rotation of the catheter in the first direction can engage one or more helical threads on an outer surface of the polymer cover with the stenosis or wall of the blood vessel, which can help advance the catheter into and eventually through the stenosis or narrowing.

These and other examples and features of the present catheters and methods will be set forth, at least in part, in the following Detailed Description. This Overview is intended to provide non-limiting examples of the present subject matter—it is not intended to provide an exclusive or exhaustive explanation. The Detailed Description below is included to provide further information about the present catheters and methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

Figure 1:
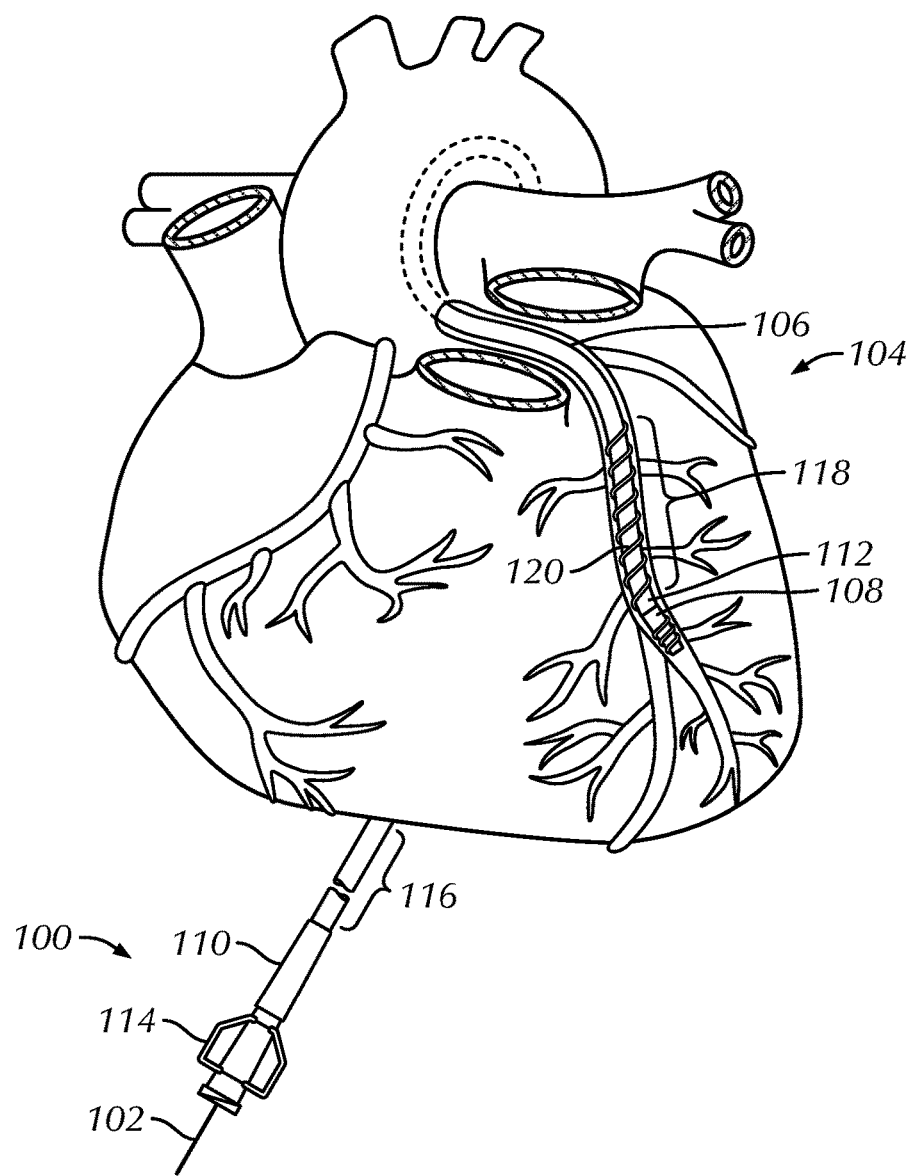
FIG. 1 illustrates a schematic view of a present catheter, as constructed in accordance with at least one embodiment, located in coronary vasculature.

The drawing figures are not necessarily to scale. Certain features and components may be shown exaggerated in scale or in schematic form and some details may not be shown in the interest of clarity and conciseness.

DETAILED DESCRIPTION

FIG. 1 illustrates a present catheter 100 for supporting a guidewire 102 or delivering a radiopaque, diagnostic or therapeutic agent through a vessel stenosis or other tortuous anatomy of coronary vasculature 104, as constructed in accordance with at least one embodiment. The present catheter 100 can be used in peripheral and coronary applications, but its primary benefit is believed to be in coronary applications where the vessels, relative to peripheral vessels, are smaller, more tortuous and more difficult to reach.

The catheter 100 can include a shaft body 106 and a tip member 108 and can be delivered through a surgically created opening in a femoral or radial artery, for example. The shaft body 106 can extend from a proximal end 110 to a distal end 112 and can define an inner lumen. The tip member 108 can be connected to the distal end 112 of the shaft body 106 and can include a lumen coaxial with the shaft body's inner lumen to facilitate receipt or delivery of the guidewire or agent. A luer hub 114 can be connected to the proximal end 110 of the shaft body 106 to facilitate connection to other medical devices, such as valves, syringes or adaptors, and to provide access to the shaft body's inner lumen.

A proximal portion 116 of the shaft body 106 can be designed to be less flexible than its distal portion 118. The less flexible proximal portion 116 can provide enhanced axial and circumferential strength to the catheter 100 for greater pushability and torqueability. The distal portion 118 can provide the catheter 100 with enhanced flexibility for negotiating winding or tortuous vascular passages. An outer surface portion of the shaft body 106, such as the distal end portion 118, can include one or more helical threads 120 to enhance catheter delivery or withdrawal through rotation.

Figure 2:
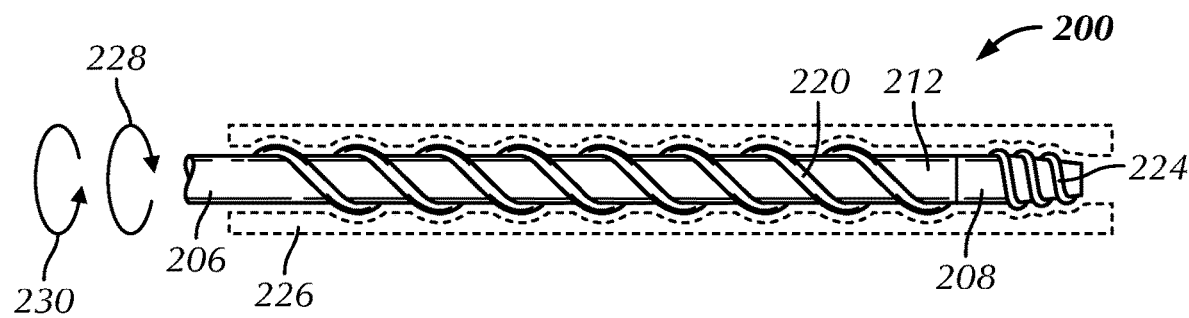
FIG. 2 illustrates a distal end portion of a present catheter, as constructed in accordance with at least one embodiment, with one or more helical threads located on both an outer surface of a shaft body and a tip member being engaged with a vessel wall.

FIG. 2 illustrates engagement between a vessel wall 226 and one or more helical threads 220, 224 projecting from outer surfaces of a catheter's shaft body 206 and tip member 208, respectively. A treating clinician can gently push the "rotate-to-advance" catheter 200 through vasculature far enough to engage the helical threads 220, 224 with the vessel wall 226. The clinician can then rotate a proximal end of the catheter 200 in the direction 228 of the helical threads, such as in a clockwise direction, to advance the catheter through small and tortuous vessels to a target site. The helical threads 220, 224 can have a sufficient radial height, relative to an outer surface of the shaft body 206 or tip member 208, to provide a longitudinal pull on the vessel wall 226 or a stenosis, if present, when rotated. The catheter 200 can be removed by rotating the proximal end of the catheter in a direction 230 opposite the direction of delivery, such as in a counterclockwise direction.

Figure 3:
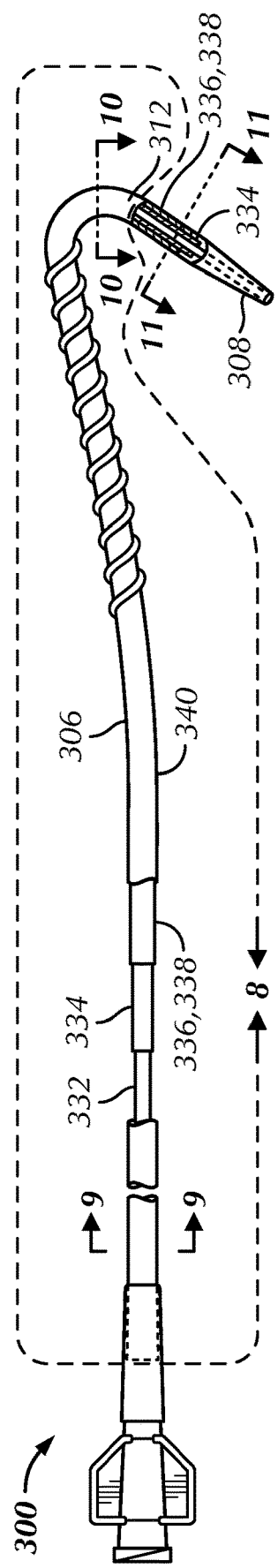
FIG. 3 illustrates partial, staggered cutaways of a present catheter, as constructed in accordance with at least one embodiment.

A side view of a catheter 300, including a shaft body 306 and a tip member 308, is illustrated in FIG. 3. The shaft body 306 can include multiple components, including an inner liner 332, a reinforcing braid member 334, two coil layers 336, 338 wound in opposing directions, and an outer polymer cover 340. The braid member 334 can be composed of multiple elongate strands having a rectangular transverse profile and arranged with its thickness directed radially. Each coil layer 336, 338 can be composed of multiple elongate stands having a fully-round transverse profile. The catheter 300 can optionally include a polymer tip member 308 composed of a non-tapered proximal portion and a tapered distal portion. The proximal portion of the tip member 308 (shown cutaway) can receive distal ends of the braid member 334 and coil layers 336, 338. Collectively, the sandwiching of the braid member 334 and coil layers 336, 338 between the inner liner 332 and the outer polymer cover 340, and the polymer tip member's 308 receipt of distal ends of the braid member 334 and the coil layers 336, 338 permits the catheter 300 to be formed at a reduced thickness while maintaining favorable structural characteristics including pushability, torqueability, flexibility and resistance to kinking.

Figure 4:
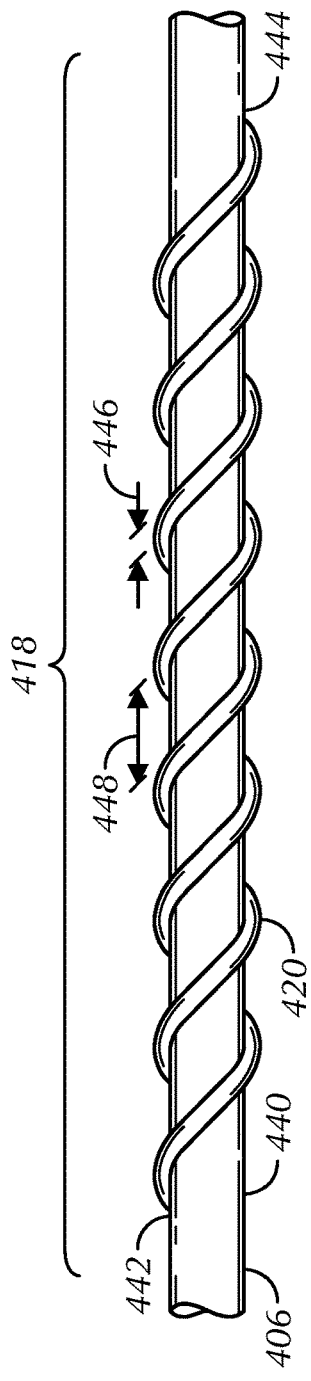
FIG. 4 illustrates an enlarged side view of a distal end portion of a present catheter's shaft body, as constructed in accordance with at least one embodiment.
Figure 5:
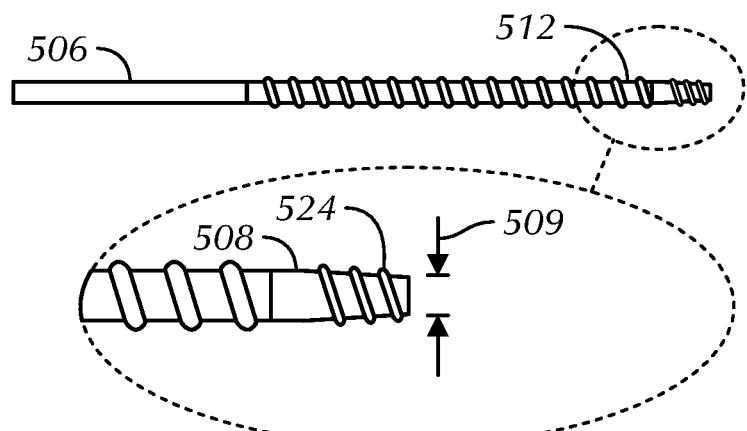
FIG. 5 illustrates a metallic tip member including one or more helical threads coupled with a distal end of a present catheter's shaft body, as constructed in accordance with at least one embodiment.
Figure 6:
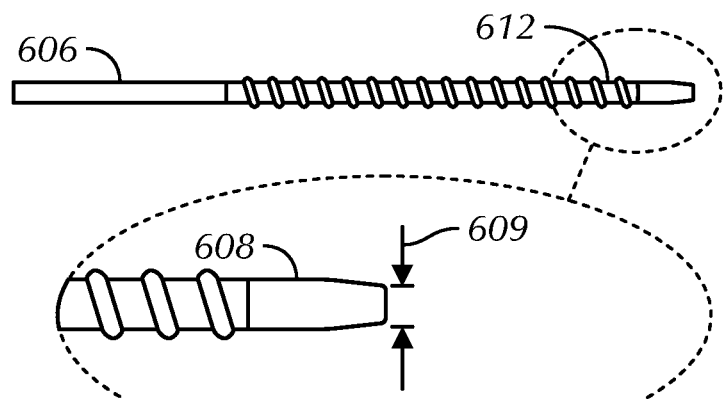
FIG. 6 illustrates a metallic tip member including a smooth outer surface coupled with a distal end of a present catheter's shaft body, as constructed in accordance with at least one embodiment.

FIG. 4 illustrates, in enlarged view, one or more helical threads 420 on an outer surface portion of a polymer cover 440, which can help propel a catheter through a blood vessel when rotated. The helical threads 420 can be positioned around a distal end portion 418 of a shaft body 406 and project radially outward. Ends 442, 444 of the helical threads 420 can be tapered from zero to full height in one-half turn of the helix to facilitate gentle, gradual displacement of a vessel wall or stenosis by the threads when the catheter is rotated for advancement and retraction. Thread width 446 and thread pitch 448 can be designed so that the vessel wall or stenosis does not bridge between adjacent turns of the threads 420 but rather is only displaced in a manner closely conforming to the threads 420, thereby providing the necessary longitudinal grip on the vessel wall or stenosis for advancing and retracting the catheter.

In various examples, the one or more helical threads 420 include a polymer member wound around the polymer cover 440. The polymer member can be a strip of a synthetic fiber, such as nylon or polyester, having a fully-round cross-sectional shape of about 0.05 mm-0.2 mm in diameter prior to being bonded to the polymer cover 440. The polymer member can have a melting temperature higher than a melting temperature of the polymer cover 440 so that the helical threads 420 can be thermally bonded to, and inlaid in, the polymer cover 440. Alternatively, the helical threads 420 can be attached to the polymer cover 440 by sonic or adhesive bonding. The polymer member can, for example, extend 20-50 turns around the outer surface of the polymer cover 440 at a uniform pitch of 1.0 mm-2.0 mm, resulting in a threaded section 2-8 cm in length. Optionally, the polymer member can be reinforced with wire or fibers.

Figure 7:
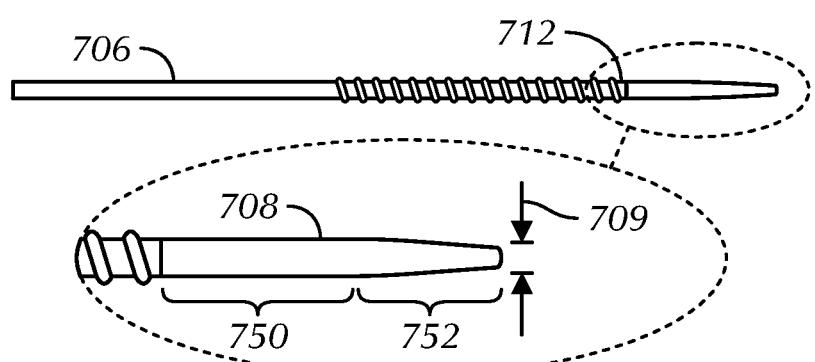
FIG. 7 illustrates a polymer tip member including a non-tapered proximal portion and a tapered distal portion coupled with a distal end of a present catheter's shaft body, as constructed in accordance with at least one embodiment.

Hard, metallic tip members or soft, polymer tip members can be utilized by the present catheters and coupled to a distal end 112, 212, 312, 512, 612, 712 of a shaft body 106, 206, 306, 506, 606, 706. FIGS. 1, 2, 5 and 6 illustrate optional metallic tip members 108, 208, 508, 608, and FIGS. 3 and 7 illustrate an optional polymer tip member 308, 708.

Metallic tip members 108, 208, 508, 608 can facilitate crossing of a difficult stenosis or other narrowing and allow for imaging on a screen as a catheter advances through vasculature. In various examples, the metallic tip member 108, 208, 508, 608 includes a gold-plated, stainless steel member available with (FIGS. 1, 2 and 5) or without (FIG. 6) one or more helical threads 224, 524. The gold-plating allows for imaging on the screen. The helical threads 224, 524 can provide rotational advancement (in additional to the helical threads of the shaft body) through a vessel stenosis or other tortuous anatomy when the catheter is rotated. In some examples, the one or more helical threads 224, 524 extend radially outward from an outer surface of the tip member 208, 508; in other examples, the helical threads extend radially inward from the outer surface and form a helical depression. Metallic tip members 608 including a smooth outer surface (i.e., without threads) can be used in treatment cases benefiting from minimized friction during catheter advancement. In various examples, a proximal diameter of the metallic tip members can be in a range of 0.8 mm to 1.10 mm and a distal diameter 509, 609 can be in a range of 0.50 mm to 0.80 mm, such as about 0.70 mm.

Polymer tip members 308, 708 can facilitate tracking through tortuous vasculature using their inherent flexibility and low profile, including a distal diameter 709 in a range of 0.3 mm to 0.6 mm. In the example of FIG. 7, the polymer tip member 708 includes a non-tapered proximal portion 750 and a tapered distal portion 752. The proximal portion 750 and the distal portion 752 can have a similar length, or the proximal portion 750 can be longer than the distal portion 752. In an example, the polymer tip member 708 has a length of 11 mm, including a 6 mm proximal portion 750 and a 5 mm distal portion 752. The polymer tip member 708 can be impregnated with a radiopaque filler material, such as barium sulfate, bismuth trioxide, bismuth carbonate, powdered tungsten, powdered tantalum or the like, so that its location within a subject's body can be radiographically visualized.

Figure 8:
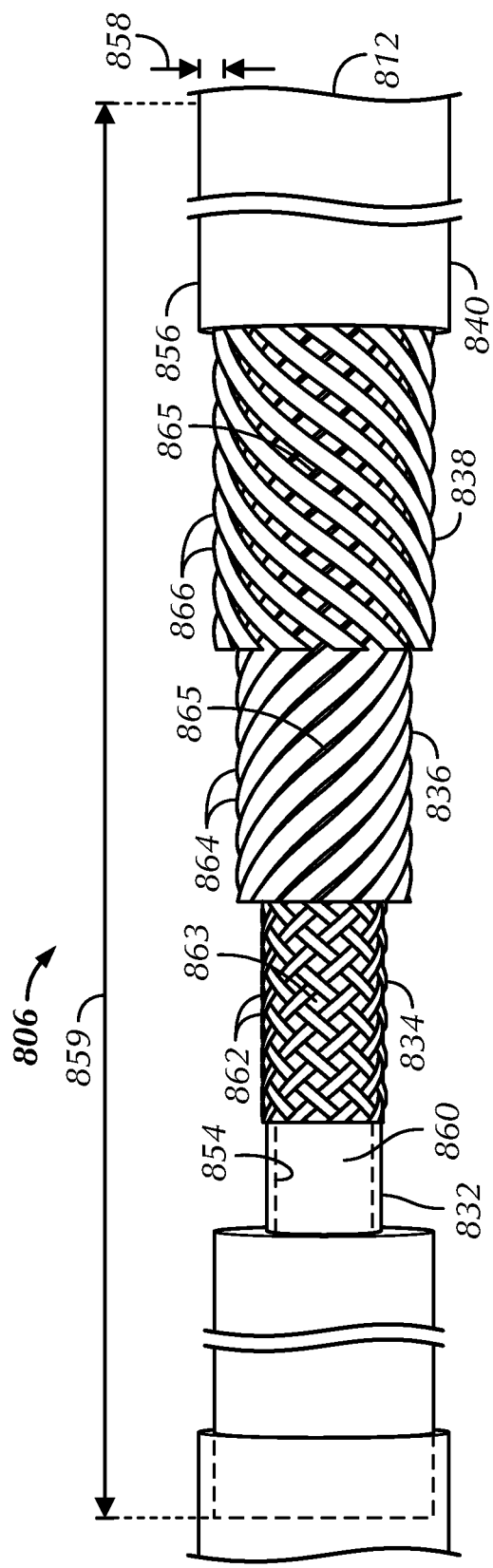
FIG. 8 illustrates partial, staggered cutaways of portions of a present catheter's shaft body, as constructed in accordance with at least one embodiment.

FIG. 8 further illustrates the multiple components of a present catheter's shaft body 806, including a liner 832, a braid member 834, multiple coil layers 836, 838 and a polymer cover 840. The shaft body 806 can define an inner lumen 860 and have an inner surface 854, an outer surface 856, a wall thickness 858 in a radial direction, and a length 859 of 60 cm-200 cm, for example.

The liner 832 can extend the length of the shaft body 806 and, optionally, into and through the catheter's tip member. The liner 832 can be formed of a material providing high lubricity, such as polytetrafluoroethylene (PTFE) or polyethylene, to reduce the forces required to advance a guidewire or other member through an associated catheter.

Surrounding the liner 832 can be a braid member 834 formed of multiple elongate strands 862 wound helically in opposite directions and interbraided with one another to form multiple crossings. The braid member 834, like the liner 832, can extend the length of the shaft body 806 and into the catheter's tip member. The strands 862 can be formed of stainless steel or another high tensile strength material and can be axially spaced apart to define multiple pics. The axial length of the pics, as determined by the strand spacing, can be selected to influence one or more of the catheter's pushability, torqueability, flexibility and kink resistance properties. The transverse profiles of the strands 862, both as to surface area and as to the ratio of width-to-thickness, can also be selected to influence these characteristics. For example, structural strength can be increased by increasing the strand width while maintaining the same thickness. Flexibility can be increased by increasing the pic axial length. Another factor influencing the desired characteristics is the braid angle of the filament strand windings, i.e., the angle of each helical strand 862 with respect to a longitudinal central axis. Increasing the braid angle tends to increase the torqueability while reducing the pushability. In short, strands 862 and arrangements of the strands 862 can be selected to customize the present catheter properties.

In the example of FIG. 8, the braid member 834 includes 16 stainless steel strands 862 having a braid angle of 45 degrees along the axis of the catheter. Other braid angle ranges from 20 degrees to 60 degrees, for example, are also suitable. The braid member 834 can be stretched axially as it is placed upon the liner 832 during manufacture. When the coil layers 836, 838 and the polymer cover 840 are placed over the braid member 834, the braid member 834 can assume an unbiased configuration. In various examples, strands 862 of the braid member 834 can have a thickness ranging from 0.010 mm to 0.015 m, but both larger and smaller strand thicknesses can also be used. Widths of the strands 862 can also vary. Some embodiments use strand widths in the range of about 0.057 mm to 0.070 mm.

The multiple coil layers, which surround the braid member 834, can include a first coil layer 836 composed of one or more wires 864 wound in a first direction and a second coil layer 838 composed of one or more wires 866 wound in a second direction, opposing the first direction. The second coil layer 838 can be positioned around and in contact with the first coil layer 836. In use, the wires 864, 866 of the first and second coil layers 836, 838 can interlock and provide the present catheter with bi-directional torqueability and pushability capabilities. For example, if one wire 864, 866 in a coil layer has a tendency to kink or bend in use, particularly under influence of a load, the other wires 864, 866 in the same layer or the adjacent layer can support it and inhibit kinking.

The wires 864, 866 can include a fully-rounded cross-section and can vary in size, number and pitch between the first coil layer 836 and the second coil layer 838 to alter structural properties of the catheter. Wire properties can be selected to balance structural properties, such as pushability, torqueability and flexibility. In an example, each coil layer includes 12 wires having a diameter of about 0.050 mm. Each of the 12 wires can have a uniform pitch that is equal to or greater than about 0.623 mm. Adjacent wires of the 12 wire grouping can be view as having a pitch that is equal to or greater than about 0.072 mm, with a small gap distributed throughout each 12 wire grouping. The size of the pitch can depend on the diameter of the wires, the diameter of the inner lumen 860 and the number of wires in the layer.

Figure 9:
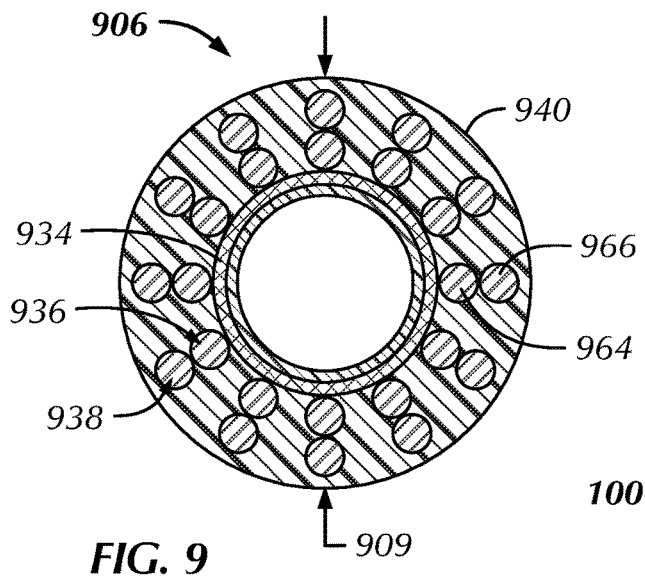
FIG. 9 illustrates a cross-section of a proximal end portion of a present catheter's shaft body, such as a cross-section along line 9-9 of FIG. 3.

The polymer cover 840 can surround the coil layers 836, 838 and, in light of the liner 832, can form the second of two polymer layers included in the shaft body 806. The polymer cover 840 can include a low-friction polymer, to reduce the forces required to advance the catheter through vasculature, or a polymer with low viscosity at melting temperatures, to allow flow through and around the coil layers 836, 838 and the braid member 834, the latter of which is shown in FIG. 9. In an example, the polymer cover 840 is composed of polyether block amide (commonly referred to as "PEBAX," a registered trademark of Arkema France Corporation). The polymer cover 840 can be applied to the coil layers 836, 838 after they are wound into a tubular shape via an extrusion, molding or shrink tubing process, and can be applied thicker along a proximal portion of the shaft body 806 than along a distal portion of the shaft body to enhance distal flexibility and provide a smaller leading size. In an example, the proximal portion includes an outer diameter 909 (see FIG. 9) between 0.9 mm-1.1 mm and the distal portion includes an outer diameter 1009 (see FIG. 10) between 0.8-1.0 mm.

A hydrophilic coating can be provided on the outer surface 856 of the shaft body 806 for lubricious delivery and to aid in steerability. The hydrophilic coating can be thin and constitute only a minor part of the wall thickness of the shaft body 806.

Figure 10:
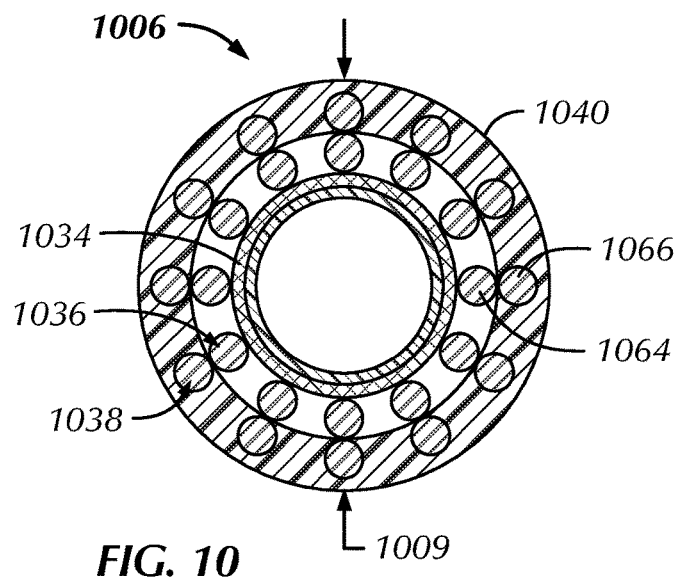
FIG. 10 illustrates a cross-section of a distal end portion of a present catheter's shaft body, such as a cross-section along line 10-10 of FIG. 3.

FIGS. 9 and 10 respectively illustrate cross-sections of a proximal portion and a distal portion of a shaft body 906, 1006, such as along lines 9-9 and 10-10 of FIG. 3. As shown, a polymer cover 940, 1040 can extend inward and seal around first and second coil layers 936, 938, 1036, 1038 and a braid member 934, 1034. Inherent elasticity of the polymer cover 940, 1040 can allow wires 964, 966, 1064, 1066 of the coil layers 936, 938, 1036, 1038 to make small movements so that the flexibility of the coil layers is maintained; the elasticity also allows the shaft body wall to stay leak-proof when the wires move. The polymer cover 940, 1040 can terminate at the distal end of the shaft body 906, 1006, proximal to a tip member.

Figure 11:
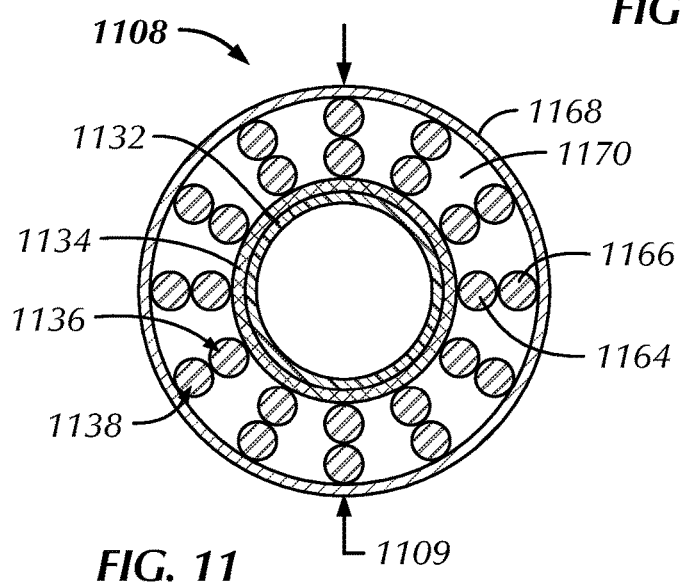
FIG. 11 illustrates a cross-section of a present catheter's polymer tip member, such as a cross-section along line 11-11 of FIG. 3.

FIG. 11 illustrates a cross-section of a proximal portion of a tip member 1108, and specifically a polymer tip member, which is coupled with a distal end of a shaft body. Distal ends of first and second coil layers 1136, 1138, a braid member 1134 and a liner 1132 can extend into the tip member 1108 and can be surrounded by a polymer impregnated with a radiopaque material. The polymer 1168 of the tip member 1108 can have a higher viscosity at melting temperatures such that little to no flow through or around the coil layers 1136, 1138 or the braid member 1134 occurs. In an example, the polymer of the tip member is pellethane and the void space 1170 existing within the polymer 1168 can provide the catheter's distal end portion with increased flexibility relative to the shaft body.

Figure 12:
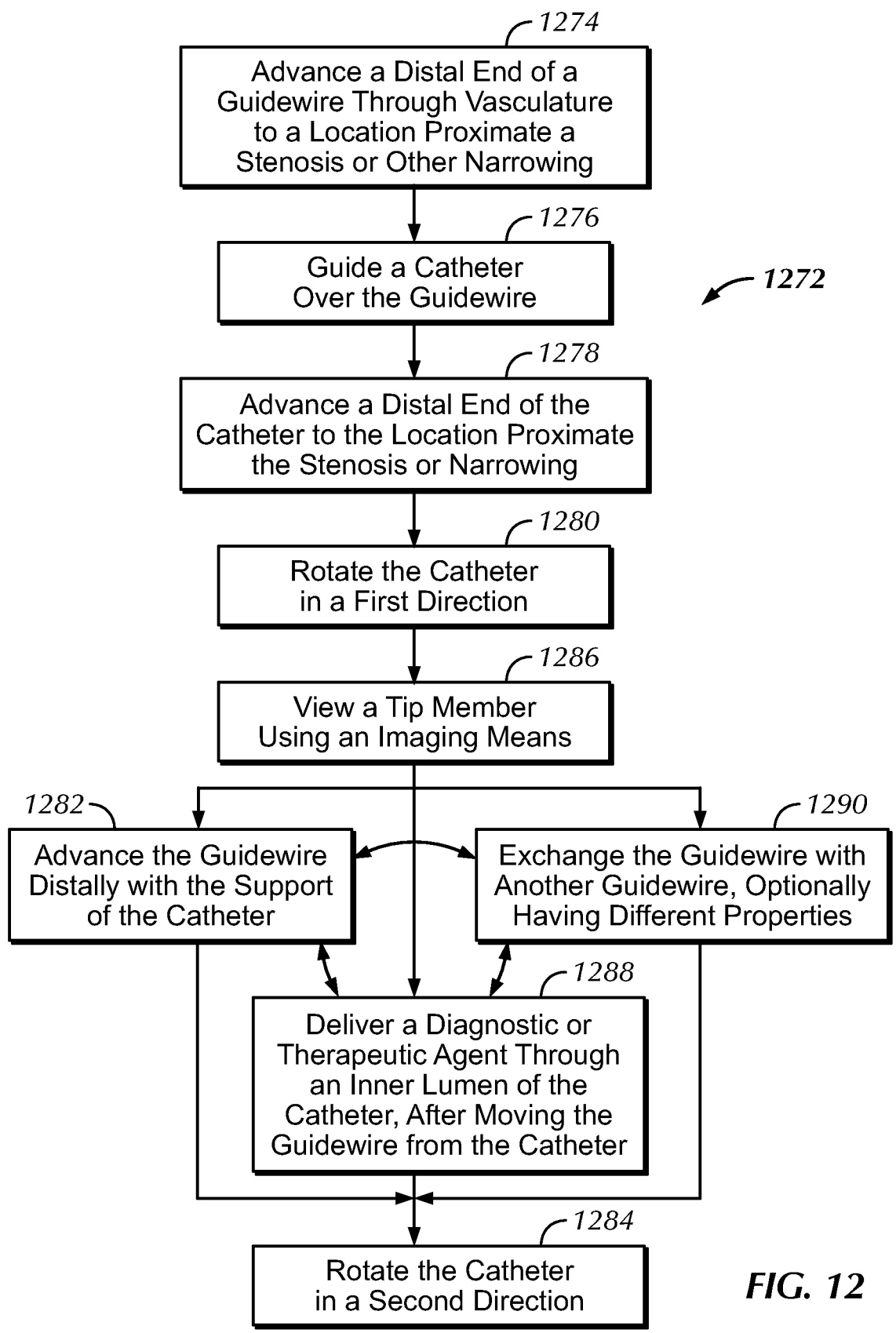
FIG. 12 illustrates a method of using a present catheter to navigate through vasculature, as constructed in accordance with at least one embodiment.

FIG. 12 illustrates a method 1272 of using a present catheter to navigate through vasculature, as constructed in accordance with at least one embodiment.

At step 1274, the method can include advancing a distal end of a guidewire through vasculature to a location proximate a stenosis or other narrowing in a blood vessel. At step 1276, a catheter can be guided over the guidewire by inserting its proximal end into an inner lumen of the catheter from the catheter's distal end. The inner lumen can be defined, in part, by a liner, a braid member surrounding the liner, a multi-layer coil surrounding the braid member, and a polymer cover surrounding the multi-layer coil. Using the guidewire as a rail, a distal end of the catheter can be advanced to the location proximate the stenosis or narrowing at step 1278.

The catheter can be rotated in a first direction at step 1280, thereby engaging one or more helical threads on an outer surface of the polymer cover with the stenosis or wall of the blood vessel. This engagement between the helical threads and the stenosis or vessel wall can propel the catheter forward, in a distal direction. Incremental rotation of the catheter, particularly the catheter's proximal end, can allow incremental movement of the catheter relative to the stenosis or vessel wall.

At step 1282, the guidewire can be advanced distally with the support of the catheter. The method can be configured such that the distal end of the guidewire is at all times distal to the distal end of the catheter.

The catheter can be withdrawn from the blood vessel at step 1284 by rotating its proximal end in a second direction, opposite the first direction. Rotation of the catheter, whether in the first direction or the second direction, can cause wires of the first and second coil layers to engage.

Additional method steps are also possible. At step 1286, the method can optionally include viewing a tip member using an imaging means. At step 1288, the method can optionally include delivering a radiopaque, diagnostic or therapeutic agent through the inner lumen of the catheter. And at step 1290, the method can optionally include exchanging the guidewire advanced to the location proximate the stenosis or narrowing with a second guidewire.

Closing Notes:

The present catheters and methods include or use a multi-component shaft body, which can include one or more helical threads projecting from its outer surface. The multi-component shaft body can provide catheters with favorable structural characteristics including pushability, torqueability, flexibility and resistance to kinking. First and second helically-wound coil layers of the shaft body, for example, can provide torqueability and pushability to the catheter. A braid member can enable a small shaft body diameter for extending through a tortuous path and reaching small vessels and can further provide kink resistance. The one or more helical threads can provide the catheter with a rotationally-activated propulsion means. Accordingly, the present catheters and methods can overcome difficulties associated with placing existing "push-to-advance" catheter designs and can possess a small cross-section to navigate tortuous anatomy.

The above Detailed Description includes references to the accompanying drawings, which form a part of the Detailed Description. The Detailed Description should be read with reference to the drawings. The drawings show, by way of illustration, specific embodiments in which the present catheters and methods can be practiced. These embodiments are also referred to herein as "examples."

The above Detailed Description is intended to be illustrative, and not restrictive. For example, the above-described examples (or one or more features or components thereof) can be used in combination with each other. Other embodiments can be used, such as by one of ordinary skill in the art upon reviewing the above Detailed Description. Also, various features or components can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a catheter can comprise an elongate shaft body and a tip member disposed at a distal end of the shaft body. The shaft body can extend from a proximal end to the distal end and can define an inner lumen. The shaft body can include a liner, a multi-layer coil surrounding the liner, and a polymer cover surrounding the multi-layer coil. An outer surface portion of the polymer cover can include one or more helical threads.

In Example 2, the catheter of Example 1 can optionally be configured such that the multi-layer coil includes a first coil layer wound in a first direction and a second coil layer, surrounding the first coil layer, wound in a second direction opposing the first direction.

In Example 3, the catheter of Example 2 can optionally be configured such that the first and second coil layers each include a plurality of wound wires having a fully round cross-section.

In Example 4, the catheter of any one or any combination of Examples 1-3 can optionally be configured such that the polymer cover extends inward through voids between successive windings of the multi-layer coil.

In Example 5, the catheter of any one or any combination of Examples 1-4 can optionally be configured such that the shaft body further comprises a braid member extending between the liner and the multi-layer coil.

In Example 6, the catheter of Example 5 can optionally be configured such that the polymer cover extends inward through voids between successive windings of the multi-layer coil and into voids of the braid member.

In Example 7, the catheter of any one or any combination of Examples 5 or 6 can optionally be configured such that a distal end of each of the liner, the braid member, and the multi-layer coil extend beyond the distal end of the shaft body.

In Example 8, the catheter of any one or any combination of Examples 1-7 can optionally be configured such that the one or more helical threads are positioned around a distal end portion of the shaft body.

In Example 9, the catheter of any one or any combination of Examples 1-8 can optionally be configured such that the one or more helical threads include a polymer member wound around the polymer cover.

In Example 10, the catheter of Example 9 can optionally be configured such that the polymer member forming the one or more helical threads has a melting point higher than a melting point of the polymer cover surrounding the multi-layer coil.

In Example 11, the catheter of any one or any combination of Examples 1-9 can optionally be configured such that the one or more helical threads include a depression of the outer surface of the polymer cover.

In Example 12, the catheter of any one or any combination of Examples 1-11 can optionally be configured such that the tip member includes a metallic tip member.

In Example 13, the catheter of Example 12 can optionally be configured such that an outer surface of the metallic tip member includes one or more helical threads.

In Example 14, the catheter of Example 13 can optionally be configured such that the one or more helical threads of the metallic tip member project radially outward from its outer surface.

In Example 15, the catheter of Example 13 can optionally be configured such that the one or more helical threads of the metallic tip member extend radially inward from its outer surface.

In Example 16, the catheter of any one or any combination of Examples 1-15 can optionally be configured such that the tip member includes a polymer tip member.

In Example 17, the catheter of Example 16 can optionally be configured such that the polymer tip member includes a non-tapered proximal portion and a tapered distal portion.

In Example 18, the catheter of Example 17 can optionally be configured such that a distal end of the multi-layer coil extends beyond the distal end of the shaft body and into the non-tapered proximal portion of the polymer tip member.

In Example 19, a method can comprise advancing a distal end of a guidewire to a location proximate a stenosis or other narrowing in a blood vessel; guiding a catheter over the guidewire; using the guidewire as a rail, advancing a distal end of the catheter to the location proximate the stenosis or narrowing; rotating the catheter in a first direction and advancing it into the stenosis or narrowing; and advancing the guidewire through the stenosis or narrowing with the support of the catheter. The guidewire can be inserted into an inner lumen of the catheter, where the inner lumen is defined, in part, by a liner, a braid member surrounding the liner, a multi-layer coil surrounding the braid member, and a polymer cover surrounding the multi-layer coil. Rotation of the catheter in the first direction can engage one or more helical threads on an outer surface of the polymer cover with the stenosis or wall of the blood vessel, which can help advance the catheter into and eventually through the stenosis or narrowing.

In Example 20, the method of Example 19 can optionally be configured such that rotating the catheter in the first direction further includes engaging one or more helical threads of a tip member, disposed at the distal end of the catheter, with the stenosis or wall of the blood vessel.

In Example 21, the method of any one or any combination of Examples 19 or 20 can optionally be configured such that rotating the catheter in the first direction includes rotating a proximal end portion of the catheter, thereby causing the distal end of the catheter to rotate a corresponding amount.

In Example 22, the method of any one or any combination of Examples 19-21 can optionally further comprise rotating the catheter in a second direction, opposite the first direction, and withdrawing the catheter from the blood vessel.

In Example 23, the method of Example 22 can optionally be configured such that rotating the catheter in the first or second direction includes engaging first and second coil layers of the multi-layer coil.

In Example 24, the method of any one or any combination of Examples 22 or 23 can optionally be configured such that rotating the catheter in the first or second direction includes inhibiting kinking between a distal end of a shaft body and a proximal end of a tip member by extending the braid member and the multi-layer coil beyond the distal end of the shaft body and into the proximal end of the tip member.

In Example 25, the method of any one or any combination of Examples 19-24 can optionally further comprise delivering a radiopaque, diagnostic or therapeutic agent through the inner lumen of the catheter.

In Example 26, the method of any one or any combination of Examples 19-25 can optionally further comprise viewing a tip member, disposed at the distal end of the catheter, using an imaging means.

In Example 27, the method of any one or any combination of Examples 19-26 can optionally further comprise exchanging the guidewire advanced to the location proximate the stenosis or narrowing with a second guidewire.

In Example 28, the catheter or method of any one or any combination of Examples 1-27 can optionally be configured such that all features, components, operations or other options are available to use or select from.

Certain terms are used throughout this patent document to refer to particular features or components. As one skilled in the art appreciates, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method, comprising:
   guiding a catheter having a shaft body and a tip member having a smooth outer surface and increased flexibility relative to the shaft body over a guidewire, including inserting a proximal end of the guidewire into an inner lumen of the catheter, where the inner lumen is defined along a length of the shaft body by a liner, a braid member, a coil member extending over the braid member, and an outer polymer cover, where the braid member includes a plurality of interbraided, metallic elongate strands along its length that form multiple strand crossings, where the coil member and the braid member extend beyond a distal end of the shaft body and into a proximal end of the tip member, and where the coil member includes one or more helically wound elongate strands composed of a same material composition at each of a proximal end of the shaft body, the distal end of the shaft body, and the proximal end of the tip member;
   using the guidewire as a rail, advancing a distal end of the catheter to a location proximate a stenosis or narrowing in a blood vessel;
   rotating the catheter in a first direction, including engaging one or more helical threads projecting relative to and surrounding an outer surface of the outer polymer cover of the shaft body with the stenosis or wall of the blood vessel, thereby advancing the catheter into the stenosis or narrowing; and
   advancing the guidewire through the stenosis or narrowing.

2. The method of claim 1, wherein inserting the proximal end of the guidewire into the inner lumen of the catheter includes inserting the proximal end of the guidewire into the tip member through which the liner extends.

3. The method of claim 1, wherein advancing the distal end of the catheter to the location proximate the stenosis or narrowing in the blood vessel includes advancing the tip member having a non-tapered proximal portion and a tapered distal portion.

4. The method of claim 1, wherein engaging the one or more helical threads with the stenosis or wall of the blood vessel includes engaging the distal end of the shaft body with the stenosis or wall of the blood vessel.

5. The method of claim 1, wherein engaging the one or more helical threads with the stenosis or wall of the blood vessel includes engaging a polymer member forming the one or more helical threads that are wound around the outer surface of the outer polymer cover of the shaft body with the stenosis or wall of the blood vessel.

6. The method of claim 5, wherein a projecting height of the polymer member increases from zero to full height within one revolution around the outer surface of the polymer cover.

7. The method of claim 5, wherein the polymer member extends around the outer polymer cover at a uniform pitch of 1.0 mm-2.0 mm.

8. The method of claim 1, wherein advancing the guidewire through the stenosis or narrowing includes advancing the guidewire through a stenosis or narrowing in a peripheral vessel.

9. The method of claim 1, wherein advancing the guidewire through the stenosis or narrowing includes advancing the guidewire through a stenosis or narrowing in a cardiac vessel.

10. The method of claim 1, further comprising exchanging the guidewire with a second guidewire.

11. The method of claim 1, further comprising viewing a position of the tip member in the blood vessel.

12. The method of claim 1, further comprising delivering a radiopaque, diagnostic or therapeutic agent through the inner lumen of the catheter.

13. A method, comprising:
    guiding a catheter having a shaft body and a tip member over a guidewire, including inserting a proximal end of the guidewire into an inner lumen of the catheter, where the inner lumen is defined along a length of the shaft body by a liner, a braid member, a coil member extending over the braid member, and an outer polymer cover, where the braid member includes a plurality of interbraided, metallic elongate strands along its length that form multiple stand crossings, where the coil member and the braid member extend beyond a distal end of the shaft body and into a proximal end of the tip member, and where the coil member includes one or more helically wound elongate strands composed of a same material composition at each of a proximal end of the shaft body, the distal end of the shaft body, and the proximal end of the tip member;
    using the guidewire as a rail, advancing a distal end of the catheter to a location proximate a stenosis or narrowing in a blood vessel;

rotating the catheter in a first direction, including inhibiting kinking between the distal end of the shaft body and the proximal end of the tip member by way of the coil member extending beyond the distal end of the shaft body and into the proximal end of the tip member; and advancing the guidewire through the stenosis or narrowing.

14. The method of claim 13, wherein rotating the catheter in the first direction further includes engaging one or more helical threads of the tip member with the stenosis or wall of the blood vessel.

15. The method of claim 13, wherein rotating the catheter in the first direction includes rotating a proximal portion of the shaft body, thereby causing the distal end of the shaft body and the tip member to rotate a corresponding amount.

16. The method of claim 13, wherein the coil member includes a first coil layer and a second coil layer, the second coil layer surrounding the first coil layer.

17. The method of claim 16, further comprising rotating the catheter in a second direction, opposite the first direction, and withdrawing the catheter from the blood vessel.

18. The method of claim 17, wherein rotating the catheter in the first or second direction includes engaging the first and second coil layers of the coil member.

19. The method of claim 18, wherein the first coil layer is wound in a first winding direction and the second coil layer is wound in a second winding direction.

20. The method of claim 18, wherein engaging the first and second coil layers includes interlocking the first and second coil layers.

21. The method of claim 13, wherein rotating the catheter in the first direction includes engaging one or more helical threads projecting relative to and surrounding an outer surface of the outer polymer cover of the shaft body with the stenosis or wall of the blood vessel, thereby advancing the catheter into the stenosis or narrowing.

* * * * *